United States Patent [19]
Kirsch et al.

[11] Patent Number: 5,921,456
[45] Date of Patent: Jul. 13, 1999

[54] SETTING TOOL FOR NAILS

[75] Inventors: Axel Kirsch, Filderstadt; Walter Duerr, Remchingen, both of Germany

[73] Assignee: Axel Kirsch, Filderstadt, Germany

[21] Appl. No.: 08/887,420

[22] Filed: Jul. 2, 1997

[30] Foreign Application Priority Data

Jul. 3, 1996 [DE] Germany ............... 196 26 892

[51] Int. Cl.⁶ ........................................ B25C 1/02
[52] U.S. Cl. .................. 227/147; 227/132; 227/156; 81/44; 173/124
[58] Field of Search .................. 227/134, 181.1, 227/147, 132, 156; 173/91, 124; 606/104, 67, 99, 100; 81/44

[56] References Cited

U.S. PATENT DOCUMENTS

| | | | |
|---|---|---|---|
| 843,655 | 2/1907 | Adell | 81/44 |
| 1,572,046 | 2/1926 | Seiler | 81/44 |
| 1,699,519 | 1/1929 | Brown | 81/44 |
| 2,384,707 | 9/1945 | Sweet | 81/44 |
| 2,594,901 | 4/1952 | Forster | 173/91 |
| 3,172,204 | 3/1965 | Frey | 81/41 |
| 3,177,952 | 4/1965 | West | 173/91 |
| 3,279,044 | 10/1966 | Roper | 81/44 |
| 4,562,948 | 1/1986 | Floyd | 227/147 |
| 4,611,739 | 9/1986 | Rowton | 227/147 |
| 4,682,412 | 7/1987 | Pfeffer | 227/132 |
| 5,492,452 | 2/1996 | Kirsch et al. | |
| 5,529,234 | 6/1996 | Juneau | 227/147 |
| 5,544,552 | 8/1996 | Kirsch | 81/44 |

*Primary Examiner*—Scott A. Smith
*Assistant Examiner*—James P. Calve
*Attorney, Agent, or Firm*—Hill & Simpson

[57] ABSTRACT

A setting tool for nails comprises a hollow cylindrical grip sleeve open at both ends with a first hollow section connected by a through-opening to a second hollow section, a ram being disposed in the first hollow section and having one end with an arrangement for releasably holding a nail extending from a first end of the grip sleeve, a pin being disposed in the first hollow section between the ram and the through-opening, the pin having a first segment connected by a centering section to a second segment which extends through the through-opening, a coupling member having a blind bore of the diameter of the second segment being disposed in the second hollow section, with the blind bore facing the pin and being urged toward the pin by a compression spring disposed in the second hollow section entrapped between the coupling member and an adjustable device. Thus, when the ram is engaged on a surface and pushed into the hollow sleeve, the pin pushes the coupling member against the compression spring until the centering section enters the through-opening to cause the axis of the pin to become aligned with the axis of the blind bore to enter the blind bore to release the coupling member to impact the pin and ram to set the nail.

12 Claims, 2 Drawing Sheets

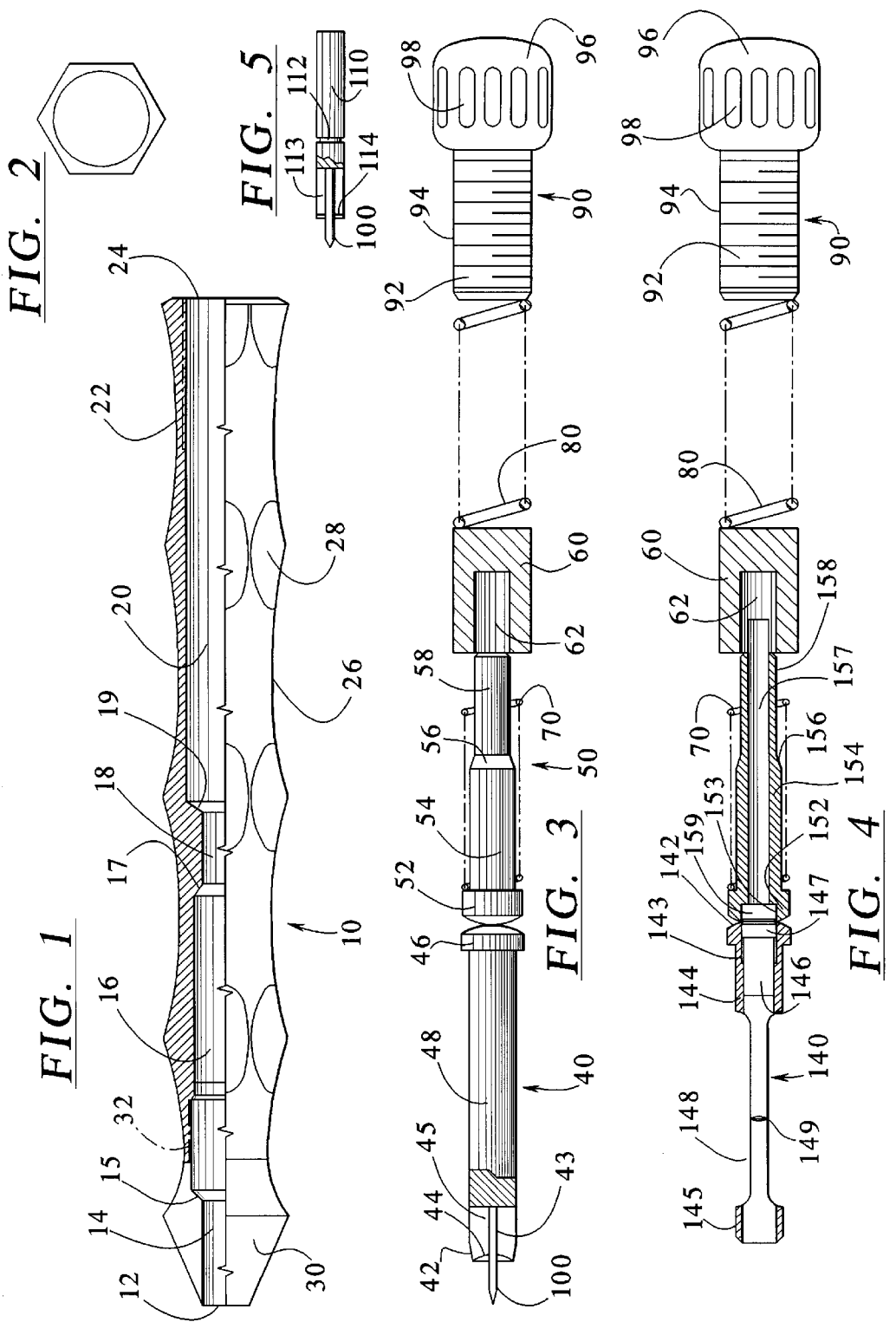

5,921,456

SETTING TOOL FOR NAILS

BACKGROUND OF THE INVENTION

The present invention is directed to a setting tool for a nail or the like, for example fastening nails for body-proper bones.

U.S. Pat. No. 5,492,452, whose disclosure is incorporated herein by reference thereto and which claims priority from German Application 43 00 039, discloses a setting tool which is composed of an elongated, pencil-like grip part having one end provided with a pressure/impact head and the other end having retaining means for a fastening nail, which is used for fastening a cover membrane to a bone having a bone void. The retaining means for the fastening nail is provided with at least two resilient gripper jaws. The operator grasps the setting tool by hand and either presses the fastening nail into the bone or strikes the impact head of the tool with a hammer to drive the fastening nail into the bone.

SUMMARY OF THE INVENTION

The object of the present invention is to provide a setting tool for nails or the like with which hitting with a hammer can be eliminated.

This object is achieved by a setting tool comprising a hollow cylindrical grip sleeve which is opened at both ends and has a first hollow section of the sleeve connected to a second hollow section by a through-opening with a reduced diameter; a ram in which a nail can be directly or indirectly releasably held is disposed in the first hollow section and extends out of a first opening; a pin, which is surrounded by a first coil spring having an axis offset from the axis of the grip sleeve, is also disposed in the first hollow section, said pin has a seating section of a first pin segment lying against the ram, a centering surface is provided in the transition region between a first pin segment and a second pin segment with the second pin segment having a diameter less than the diameter of the through-opening and extending therein; a cylindrical coupling piece is disposed in the second hollow section and has a blind hole or bore of the diameter of the second pin segment facing the through-opening; an adjustment means is disposed in the other end and a second coil spring is entrapped between the adjustment means and the coupling piece to urge the coupling piece toward the through-opening.

Advantageously, the pin has a seating section engaging a seating section of the end of the ram, and the seating sections are both fashioned to have convex curvature in their contacting region. In the invention, the free end of the ram can be fashioned as a holder for the head of a nail and has gripping or holding means, such as disclosed in the above-mentioned U.S. Patent.

In a development of the invention, the ram and pin are hollow-cylindrically fashioned so that the insides can accommodate a second pin, the length of said inside or second pin being greater than the length of the hollow pin and the inside pin acting directly or indirectly on a nail holder that is inserted into the hollow ram. Preferably, a coupling pin is accommodated in the hollow-cylindrical ram.

The hollow ram can also have a viewing window that allows a view of the nail holder. It is especially preferred that the hollow ram has a catch means for engaging the nail holder.

Expediently, the adjustment device can be an adjustment screw, whose threaded section engages internal threads provided in the grip sleeve adjacent the second end.

A hammer or similar impact tool is no longer needed for this spring-operated setting tool. The impact force is defined by the energy stored in the compressed, second coil spring and a modification of the impact force is produced in that the adjustment device prestresses the spring to a greater or lesser extent.

Other advantages and features of the invention will be readily apparent from the following description of the preferred embodiments, the drawings and claims.

BRIEF DESCRIPTION OF THE DRAWINGS

FIG. 1 is a side view partially broken away to illustrate the grip sleeve of the setting tool according to the present invention;

FIG. 2 is an end view of the grip sleeve of FIG. 1;

FIG. 3 is a side view with portions broken away in cross section of a first embodiment of an impact spring mechanism for the setting tool according to the present invention;

FIG. 4 is a side view with portions broken away for purposes of illustration of a second embodiment of the impact spring mechanism;

FIG. 5 is a side view with portions broken away of an example of a nail holder utilized with the embodiment of FIG. 4;

DESCRIPTION OF THE PREFERRED EMBODIMENTS

Figure 6:
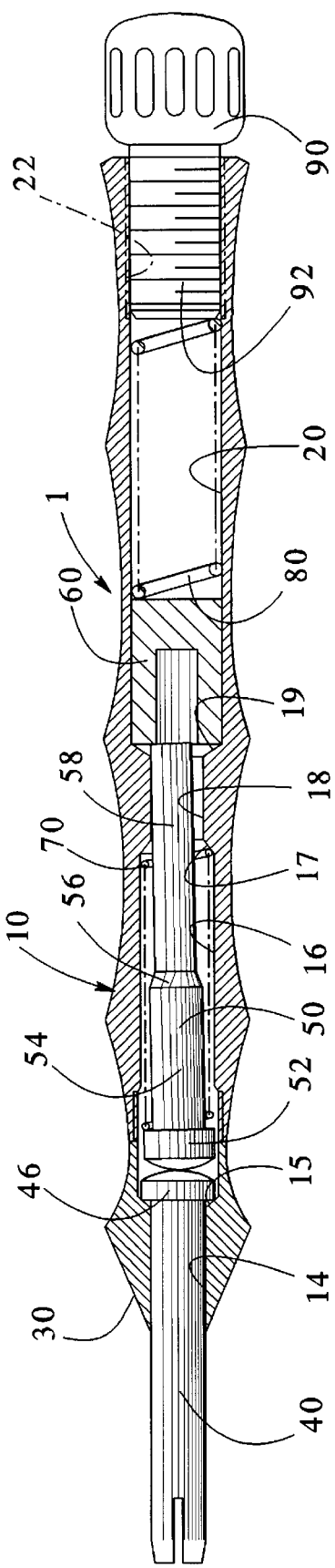
FIG. 6 is a cross sectional view with portions in elevation of the setting tool of the first embodiment.

The principles of the present invention are particularly useful when incorporated into a setting tool, generally indicated at 1 in FIG. 6. The tool 1 has a grip sleeve, generally indicated at 10 in FIGS. 1 and 6, and an impact spring mechanism, best illustrated in FIG. 3.

The grip sleeve 10 (FIG. 1) is essentially a hollow-cylindrical tube with two open ends 12 and 24. At the end 12, an opening section 14 extends into a first hollow section 16 and then through a through-opening 18 of a smaller diameter to a second hollow section 20. An inside or internal thread 22 is provided in a part of the second hollow section adjacent the open end 24. The outside contour of the grip sleeve is essentially determined in an ergonomic point of view. A hexagonally symmetrical design, as indicated by the end view of FIG. 2, has proved expedient. Holding depressions, for example at 26, and finger depressions, for example at 28, are provided on the outside of the grip sleeve 10. A front part 30 of the grip sleeve can be screwed into a thread 32 provided in the first hollow section 16.

Figure 7:
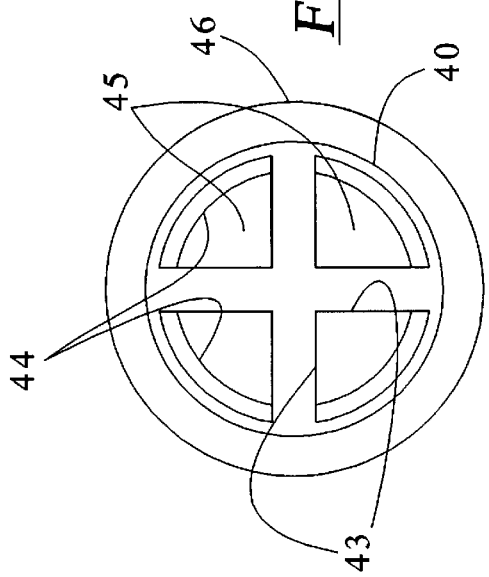
FIG. 7 is an end view of the ram of the first embodiment.

An impact spring mechanism is inserted into this grip sleeve 10, as illustrated in FIG. 6. The first embodiment of the impact spring mechanism shown in FIG. 3 is composed of a ram 40, a pin 50, which has a first coil spring 70 disposed therearound, a coupling piece or member 60, a second coil spring 80 and an adjustment screw 90. The ram 40 and the pin 50 are at least partially accommodated in the first hollow section, wherein the ram 40 has a portion projecting through the opening section 14 and out of the open end 12. A holder mechanism or means for a nail 100 is arranged on the end of the ram 40. This holder means is composed of preferably four gripper jaws 45 (FIG. 7) that have a bevel or recess at their side facing away from the grip sleeve 10 and that overall form a seating shoulder 44 for the head of the nail 100. The four jaws 45 are separated by intersecting slots 43 and spread apart at these slots 43 by the head of the nail with the amount of spreading being dependent on the size of the nail head. It is noted that this gripping means of the gripper jaw is basically the same structure as that illustrated and set forth in the above-mentioned U.S. Pat. No. 5,492,452.

The holding mechanism or holder means is joined by a shaft 48 that ends in a seating section or head 46, whose outside dimensions are selected to be larger than the diameter of the shaft. The seating section 46 defines a first seating shoulder for an obliquely proceeding annular shoulder 15 between the opening 14 and the first hollow section 16.

A similarly-design second seating section 52 of a pin 50 lies against the seating section 46, which has a convex contact surface. The convex contact surface of the two seating sections 46 and 52 allow the axes of the ram and pin to be tilted relative to one another. Since the ram 40 is guided through the opening 14 in the grip sleeve, the axis of the ram 40 is aligned with the axis of the grip sleeve 10, and this means that the axis of the pin 50 can be tilted relative to the axis of the grip sleeve 10, as illustrated in FIG. 6. This tilting is compelled with the assistance of a coil spring 70 that is placed around the pin 50, whereby it will lie against a first pin segment or section 54 adjoining the seating or head section 52. A conically tapering centering surface or section 56 forms a transition to a second pin section or segment 58 that correspondingly has a smaller diameter than the pin segment 54. The coil spring 70 does not lie against the second pin segment 58. The end of the pin segment 58, which is not surrounded by the coil spring, will project through the opening 18, and it is noted that it has a diameter that is less than the diameter of the opening 18. With the pin 50 disposed in the first hollow chamber 16, it is noted that the end of the spring 70 bears against the centering shoulder 17 between the first hollow chamber 16 and the through-opening 18. It is also noted that the diameter of the through-opening 18 is approximately the same as the first pin segment 54 so that the first pin segment 54 can be slidably received therein.

The coupling piece 60 is provided in the second hollow section 20 of the grip sleeve 10, and has a blind hole or bore 62 which faces toward the opening 18. The blind hole 62 has a diameter equal to the diameter of the second section 58 of the pin so that the pin can be slidably received in the blind hole 62. A coil spring 80 is disposed in the second hollow section 20 and bears against one end of the coupling piece 60 to hold it against the shoulder 19 of the grip sleeve. The other end of the spring engages an end of a shaft 92 with threads 94 of the adjustment means 90. The adjustment means 90 is, thus, threaded by the threads 94 on the shaft portion 92 being threaded into the internal threads 22 of the grip sleeve. To facilitate the threading, a head 96 of the adjustment means is provided with gripping grooves 98. Depending on the amount of threading of the member 90 into the threads 22, the amount of compression or prestressing of the second coil spring 80 can be changed.

When tensioning the system, the ram-pin arrangement 40, 50 is pushed farther into the grip sleeve 10. Since the coil spring 70 is offset relative to the axis of the grip sleeve 10, the second pin segment 58, whose axis is likewise forced into an offset position by the coil spring 70, it will engage an edge of the blind hole 62. As a result, the coupling piece 60 is urged against the coil spring 80, which is then compressed farther. The movement and compression of the spring 80 continues until a centering surface 56 moves into the region of the conical surface 17 that connects the first hollow section 16 and the through-bore 18. When the centering surface 56 moves into the conical surface 17, the pin is forcibly centered so that the second segment 58 suddenly is aligned with the blind hole 62 and suddenly enters the hole. As soon as the second pin segment is aligned with the hole 62, it is entered into the hole and the spring 80 moves the coupling member 60 until the floor or base of the blind hole 62 hits the end of the pin to cause an impact which is executed in the direction toward the ram 40 to insert the nail 100. Thus, the coupling member 60 provides a hammer blow on the pin 50, which transfers this blow to the ram 40.

An embodiment or modification of the spring impact mechanism is illustrated in FIGS. 4 and 5. In this modification, a ram 140 is fashioned as a hollow cylinder into which a coupling pin 146 is inserted at an end that faces toward a pin 150. A nail holder shown in FIG. 5 is introduced into the ram 140 so that it lies against the end of the coupling pin 146. The nail holder has a catch channel 112 which is engaged in a corresponding catch rib 149 that is provided at a corresponding location on the inside circumference or bore of the ram 140, so that the catch channel 112 forms catch means for engaging the rib 149 of the nail holder. Through viewing windows, such as 148, that are provided in the walls of the ram 140, one can ascertain whether the nail holder 110 has been correctly placed in the ram 140. A nail 100 is again held in the nail holder 110 by a holding means that is described above and has gripping jaws, such as 113, that hold the head of the nail 100 on a seating shoulder 114. The end of the nail holder 110 with the nail 100 is surrounded by an end region 145 of the ram 140. At an end facing toward the pin 150, the coupling pin 146 has an enlarged head 147 that can slide in an enlarged inside recess 143 of the ram 140 and whose axial movement is limited by this ram.

The pin 150 is likewise fashioned as a hollow pin, wherein the outside contour has a first pin section or segment 154, a centering surface or section 156 and a second pin segment or section 158, which are dimensioned as in the first-mentioned embodiment of FIG. 3. A coil spring 70 is also arranged in the same way. In particular, the axis of the pin 150 will be offset relative to the axis of the grip sleeve 10. An inside or inner pin 157, whose head 159 is seated in a seating recess 153 of the pin 150, is accommodated in the pin 150. The inside pin 157 can thus move only in the direction of the ram 140. The inside pin 157 projects farther beyond the second pin section 158 and into a blind hole 62 of the coupling piece 60. The arrangement of the ram 140 and the pin 150 with the coupling member or piece 60, of the coil spring 80 and of the adjustment screw 90 in the grip sleeve 10 corresponds to that of the first embodiment.

The fundamental difference of the second embodiment of FIG. 4 over the embodiment of FIG. 3 is that the tensioning system of the force is not applied on the nail 100 but is applied to the hollow ram 140. This prevents the nail 100 from canting or, respectively, falling out prematurely. Thus, during the pressing of the piece against the bone, the end 145 is surrounding the end of the nail 100. In addition, the impact motion is triggered when the end of the inside pin 154 projecting into the blind hole is contacted by the base of the blind hole 62 as the second section 158 is centered to enter the blind hole.

Although various minor modifications may be suggested by those versed in the art, it should be understood that we wish to embody within the scope of the patent granted hereon all such modifications as reasonably and properly come within the scope of our contribution to the art.

We claim:

1. A setting tool for nails comprising an essentially hollow cylindrical grip sleeve with a longitudinal axis opened at both ends, said sleeve having a first hollow section adjacent a first end, said section being connected to a second hollow section adjacent an opposite second end by a through-opening; a hollow cylindrical ram having first means for releasably holding a nail at one end, said first means being a nail holder removably received in the ram, said ram being received in the first hollow section with a portion having the first means extending from the grip sleeve through the first end; a pin being surrounded by a first coil spring being introduced in the first hollow section between the ram and the through-opening, said pin adjacent the ram having a first pin segment of a diameter receivable in the through-opening, a second pin section of a smaller diameter than the diameter of the first pin segment and a centering surface extending therebetween, said pin being formed by a hollow pin receiving an inside pin with a length greater than the length of the hollow pin, said first coil spring having an axis offset from the longitudinal axis of the grip sleeve; a cylindrical coupling piece having a blind bore of a diameter equal to the second pin segment, said cylindrical coupling piece being disposed in the second hollow section with the blind bore facing the through-opening; a second spring disposed in the second hollow section acting against the coupling piece and adjustment means closing the opposite second end for adjusting the amount of compression of said second spring, so that upon moving an exposed end of the ram against a surface causes compression of the second spring until the centering surface moves into the through-opening to cause the pin to be axially aligned with the blind bore so that the second pin section enters the blind bore to release the coupling piece to apply an impact through the pin to the ram to set the nail.

2. A setting tool according to claim 1, wherein the adjustment means is an adjustment screw having a threaded section engaged into internal threads provided in the second hollow section adjacent the opposite second end.

3. A setting tool according to claim 1, wherein a seating section of the pin facing the ram and a seating section of the ram facing the pin are convex surfaces forming a contacting region.

4. A setting tool according to claim 1, which includes a coupling pin received in the hollow ram to transfer the force from the inside pin of the pin to the nail holder.

5. A setting tool according to claim 4, wherein the ram has a viewing window.

6. A setting tool according to claim 5, wherein the ram includes a catch means for engagement with the nail holder.

7. A setting tool according to claim 6, wherein the adjustment means comprises an adjustment screw having a threaded section engaged into internal threads provided in the grip sleeve at the opposite second end.

8. A setting tool according to claim 1, wherein the ram includes a viewing window.

9. A setting tool according to claim 8, wherein the ram includes a catch means for engagement with the nail holder.

10. A setting tool according to claim 9, wherein the adjustment means includes an adjustment screw having a threaded section engaged into internal threads provided in the second hollow section of the grip sleeve adjacent the second end.

11. A setting tool according to claim 1, wherein the hollow cylindrical member of the ram includes catch means for holding the nail holder therein.

12. A setting tool according to claim 11, wherein the adjustment means has an adjustment screw with a threaded section engaged into internal threads provided in the second hollow section adjacent the opposite second end of the grip sleeve.

* * * * *